United States Patent [19]

Tremont et al.

[11] 4,443,641

[45] Apr. 17, 1984

[54] ATTRITION RESISTANT BISMUTH-CONTAINING METAL/OXYGEN COMPOSITIONS

[75] Inventors: Samuel J. Tremont, Manchester, Mo.; Robert A. Keppel, Seabrook, Tex.; Emerson H. Lee; George D. Davis, both of Creve Coeur, Mo.

[73] Assignee: Monsanto Company, St. Louis, Mo.

[21] Appl. No.: 488,562

[22] Filed: Apr. 25, 1983

Related U.S. Application Data

[62] Division of Ser. No. 335,786, Dec. 30, 1981, Pat. No. 4,409,133.

[51] Int. Cl.$^3$ .............................................. C07C 2/72
[52] U.S. Cl. ................................................... 585/428
[58] Field of Search ................ 585/428; 252/463, 464, 252/466 J

[56] References Cited

U.S. PATENT DOCUMENTS

| | | | |
|---|---|---|---|
| 3,668,151 | 6/1972 | Walker | 252/466 |
| 3,925,447 | 12/1975 | Gelbein | 260/465 |
| 4,254,293 | 3/1981 | Tremont et al. | 585/428 |
| 4,260,845 | 4/1981 | Shioyama | 585/640 |

*Primary Examiner*—Delbert E. Gantz
*Assistant Examiner*—Cynthia A. Prezlack

[57] ABSTRACT

Attrition resistant bismuth-containing metal/oxygen compositions comprising the infusion and reaction product of an alumina existing in a crystal form selected from the group consisting of $\gamma$, $\delta$, $\eta$, and $\chi$ crystal forms, and mixtures thereof or that can be transformed by heat to such crystal forms, and characterized by a mean particle size from about 10 $\mu$m to about 200 $\mu$m, a fractional porosity of at least 0.2, a surface area of at least 150 m$^2$/g, and a pore diameter such that at least 10 percent of the pores are less than 55 Å, and at least one bismuth oxide, or compound convertible by heat to such bismuth oxide, having a maximum mean particle size of about 100 $\mu$m, with the proviso that the alumina/bismuth oxide mean particle size ratio is at least 2, which bismuth oxide is susceptible of undergoing infusion and reaction with the alumina upon being subjected to temperatures of at least 0.4 $T_m$ for a time sufficient to cause infusion and reaction between the bismuth oxide and the alumina, wherein $T_m$ is the melting point of °K. of the alumina, are useful in metal oxide-catalyzed reactions which involve reaction conditions of high stress, for example, vapor phase oxidations under fluidized bed conditions. The compositions are especially useful for the dehydrocoupling of toluene to yield toluene dehydrocoupled products in high yields and selectivities.

21 Claims, No Drawings

ATTRITION RESISTANT BISMUTH-CONTAINING METAL/OXYGEN COMPOSITIONS

This is a division of application Ser. No. 335,786, filed Dec. 30, 1981, now U.S. Pat. No. 4,409,133.

CROSS-REFERENCE TO RELATED APPLICATIONS

"Attrition Resistant Metal/Oxygen Compositions", Ser. No. 335,791, 335,792, and 335,785, filed Dec. 30, 1981.

BACKGROUND OF THE INVENTION

1. Field of the Invention

This invention relates to attrition resistant bismuth-containing metal/oxygen compositions and a process for preparing such compositions. More particularly, this invention relates to bismuth-containing metal/oxygen compositions comprising the infusion and reaction product of:

(a) an alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å, and (b) at least one bismuth oxide, or compound convertible by heat to such bismuth oxide, having a maximum mean particle size of about 100 $\mu$m, with the proviso that the alumina/bismuth oxide mean particle size ratio is at least 2, which bismuth oxide is susceptible of undergoing infusion and reaction with the alumina upon being subjected to temperatures of at least 0.4 $T_m$ for a time sufficient to cause infusion and reaction between the bismuth oxide and the alumina, wherein $T_m$ is the melting point in °K. of the alumina.

The attrition resistant bismuth-containing metal/oxygen compositions of this invention may be used for any of a wide variety of purposes generally known in the art. Thus, for example, the compositions are useful in the transformation of numerous organic compounds in the vapor phase such as dehydrogenation reactions, oxidation reactions, hydrogenation reactions, isomerization reactions, dealkylation reactions, dehydrocoupling reactions, and the like. The compositions may be employed in a manner identical to that for bismuth-containing metal/oxygen compositions heretofore known in the act for such transformations.

2. Description of the Prior Art

Supported metal oxides are well-known as catalysts and oxygen carriers for a wide variety of chemical reactions. In general, such metal oxide compositions are comprised of a metal oxide coated on a support material of low porosity and low surface area. Such a support is commonly referred to as an inert support. The method generally employed to produce these supported metal oxide compositions involves impregnating the inert support with a solution of a soluble salt of the metal oxide, separating the resultant impregnated solid, and heating to remove a substantial portion of the solvent. The impregnated solid is then calcined at elevated temperatures to convert the metal salt to the corresponding metal oxide. Multiple impregnations are sometimes employed to achieve an increased concentration of metal oxide on the support.

Another well-known technique employed for forming supported metal oxide compositions involves suspending the support materials in a solution of a salt of the metal, completely or partially evaporating the solvent, and possibly mixing the resultant material with an organic binder and pelletizing thereof. The dry pellet is then heated to an elevated temperature to effect complete dehydration and burning out of the organic material.

A method for forming a supported metal oxide on a porous support is disclosed in U.S. Pat. No. 3,925,447 which involves contacting the porous support material with the metal oxide in molten form to produce a catalyst in which the metal oxide is substantially entirely within the pores of the support. The resultant catalyst is used in the production of nitriles.

U.S. Pat. No. 3,668,151 discloses a high strength (as indicated by its crush strength) zinc aluminate catalyst composition. Upon being impregnated with platinum, lithium, and tin in the usual manner, the resultant catalyst was used to dehydrogenate n-butane to olefins and diolefins, presumably 1- and 2-butene and 1,3-butadiene.

A substantially identical zinc aluminate catalyst having an approximate mole ratio of zinc oxide to alumina of 1 also is disclosed in U.S. Pat. No. 4,260,845. The catalyst is reported to be useful for dehydration of saturated alcohols to olefins, for example, 2-methyl-1-butanol to 2-methyl-1-butene.

Although these prior art compositions are generally suitable for their stated purposes, the commercial utility of catalysts and oxygen carrier compositions in reactions which involve reaction conditions of high stress (such as high temperatures and/or pressures, especially under fluidized bed conditions) require compositions which are highly resistant to abrasion and attrition due to the deleterious effects of reaction conditions. Accordingly, research efforts are continually being made for high efficiency catalyst and oxygen carrier compositions of increased physical strength and attrition resistance which are useful in reactions involving conditions of high stress. The discovery of the compositions of the present invention, therefore, is believed to be a decided advance in the catalyst and oxygen carrier composition art.

SUMMARY OF THE INVENTION

It is an object of this invention to provide attrition resistant bismuth-containing metal/oxygen compositions.

Another object of this invention is to provide attrition resistant bismuth-containing metal/oxygen compositions highly effective for the vapor phase transformation of organic compounds.

Yet another object of this invention is to provide attrition resistant bismuth-containing metal/oxygen compositions highly effective as combination catalyst/oxygen carrier compositions in the vapor phase oxidative dehydrocoupling of toluene to yield toluene dehydrocoupled products in high yields and selectivities.

Still another object of this invention is to provide a process for the preparation of attrition resistant bismuth-containing metal/oxygen compositions effective for the vapor phase transformation of organic compounds.

To achieve these and other objects which will become apparent from the accompanying description and claims, attrition resistant bismuth-containing metal/oxygen compositions are provided which comprise the infusion and reaction product of:

(a) an alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å, and
(b) at least one bismuth oxide, or compound convertible by heat to such bismuth oxide, having a maximum mean particle size of about 100 $\mu$m, with the proviso that the alumina/bismuth oxide mean particle size ratio is at least 2, which bismuth oxide is susceptible of undergoing infusion and reaction with the alumina upon being subjected to temperatures of at least 0.4 $T_m$ for a time sufficient to cause infusion and reaction between the bismuth oxide and the alumina, wherein $T_m$ is the melting point in °K. of the alumina.

The provision of the process for the preparation of such compositions object is achieved by a process which comprises:

(a) forming a mixture of alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å,
  and at least one bismuth oxide, or compound convertible by heat to such bismuth oxide, having a maximum mean particle size of about 100 $\mu$m, with the proviso that the alumina/bismuth oxide mean particle size ratio is at least 2, which bismuth oxide is susceptible of undergoing infusion and reaction with the alumina, and
(b) heating the mixture to a temperature of at least 0.4 $T_m$ for a time sufficient to cause infusion and reaction between the bismuth oxide and the alumina, wherein $T_m$ is the melting point in °K. of the alumina.

The provision of the toluene dehydrocoupling process object is achieved by a process which comprises:

(a) contacting the toluene in the vapor phase at a temperature from about 450° C. to about 650° C. with an attrition resistant bismuth-containing metal/oxygen composition comprising the infusion and reaction product of
  (i) an alumina existing in a crystal form selected from the group consisting of $\gamma$, $\delta$, $\eta$, and $\chi$ crystal forms, and mixtures thereof, or that can be transformed by heat to such crystal forms, and characterized by
    (a) a mean particle size from about 10 $\mu$m to about 200 $\mu$m,
    (b) a fractional porosity of at least 0.2,
    (c) a surface area of at least 150 m$^2$/g, and
    (d) a pore diameter such that at least 10 percent of the pores are less than 55 Å, and
  (ii) at least one bismuth oxide, or compound convertible by heat to such bismuth oxide, having a maximum mean particle size of about 100 $\mu$m, with the proviso that the alumina/bismuth oxide mean particle size ratio is at least 2, which bismuth oxide is susceptible of undergoing infusion and reaction with the alumina upon being subjected to temperatures of at least 0.4 $T_m$ for a time sufficient to cause infusion and reaction between the bismuth oxide and the alumina, wherein $T_m$ is the melting point in °K. of the alumina, and
(b) recovering the toluene dehydrocoupled product.

Other objects and advantages of the present invention will become apparent from the accompanying description and claims.

DESCRIPTION OF THE PREFERRED EMBODIMENTS

1. The Compositions

The attrition resistant bismuth-containing metal/oxygen compositions of the present invention comprise the infusion and reaction product of:

(a) an alumina existing in a crystal form selected from the group consisting of $\gamma$, $\delta$, $\eta$, and $\chi$ crystal forms, and mixtures thereof, or that can be transformed by heat to such crystal forms, and characterized by
  (i) a mean particle size from about 10 $\mu$m to about 200 $\mu$m,
  (ii) a fractional porosity of at least 0.2,
  (iii) a surface area of at least 150 m$^2$/g, and
  (iv) a pore diameter such that at least 10 percent of the pores are less than 55 Å, and
(b) at least one bismuth oxide, or compound convertible by heat to such bismuth oxide, having a maximum mean particle size of about 100 $\mu$m, with the proviso that the alumina/bismuth oxide mean particle size ratio is at least 2, which bismuth oxide is susceptible of undergoing infusion and reaction with the alumina upon being subjected to temperatures of at least 0.4 $T_m$ for a time sufficient to cause infusion and reaction between the bismuth oxide and the alumina, wherein $T_m$ is the melting point in °K. of the alumina.

The attrition resistant characteristics of the bismuth-containing metal/oxygen compositions of the present invention, preferably exhibiting an attrition rate less than 0.5 weight percent/hour, make them excellent for use in reactions which involve reaction conditions of high stress, particularly in a fluidized bed system at elevated temperatures and/or pressures.

The term "infusion" and related terms are employed herein to mean a process by which two adjacent solids of differing compositions homogenize by diffusion of one of such compositions into the other, for example, the diffusion of the bismuth oxide into the alumina.

The term "fractional porosity" is employed herein to mean the ratio of void space or volume in a particle to the bulk or total volume of that particle.

The term "attrition", as employed herein, means the art of wearing or grinding down by friction and breakage of the structures into dust and fines.

The term "attrition rate", as employed herein, means an accelerated attrition rate and refers to the rate of attrition as determined by an accelerated attrition test described in Example 3, below.

The materials suitable for use as components of the bismuth-containing metal/oxygen compositions of this invention must, of necessity, possess those properties and characteristics which yield attrition resistant compositions. In addition, the component materials advantageously should yield bismuth-containing metal/oxygen compositions which are suitable for the vapor phase transformation of organic compounds, especially the dehydrocoupling of toluene, to yield the desired products in high yields and selectivities. Such materials are available commercially from numerous catalyst and metal oxide suppliers.

Aluminas which are useful as components of the attrition resistant bismuth-containing metal/oxygen compositions are fairly wide in scope. Such materials, however, must possess certain characterizing properties to be suitable for use in the present invention. Included among such properties are (a) a mean particle size from about 10 $\mu$m to about 200 $\mu$m, and preferably from about 20 $\mu$m to about 125 $\mu$m; (b) a fractional porosity of at least 0.2, with values from about 0.2 to about 0.8 being preferred, a surface area of at least 150 m$^2$/g, and a pore diameter such that at least 10 percent, and preferably 30 percent or more, of the pores are less than 55 Å. Also, in order to facilitate ease of fluidization, the alumina particles preferably are spheroidal in shape.

Aluminas suitable for use in the present invention are those which possess the aforementioned characterizing properties and, in addition, exist predominantly in a crystal form selected from the group consisting of gamma ($\gamma$), delta ($\delta$), eta ($\eta$), and chi ($\chi$) crystal forms, and mixtures thereof, or that can be transformed by heat to these crystal forms. Included among the latter grouping are hydrated aluminas such as Boehmite, pseudo-Boehmite, Bayerite, and Gibbsite.

Bismuth oxides suitable for use within the scope of the present invention are those commonly known to the art. Such bismuth oxides must, of necessity, be susceptible of undergoing infusion and reaction with the alumina under conditions hereinafter described to yield the attrition resistant bismuth-containing metal/oxygen composition. In addition, the bismuth oxide must have a maximum mean particle size of about 100 $\mu$m, with the proviso that the alumina/bismuth oxide mean particle size ratio is at least 2, and preferably 15 or more. The stated mean particle size ratio permits the bismuth oxide and the alumina to undergo the desired infusion and reaction with little, if any, material change in the original particle size of the alumina. This phenomenon results in the high strength attrition resistant bismuth-containing metal/oxygen compositions of this invention.

Suitable bismuth oxides are exemplified by bismuth (III) oxide (Bi$_2$O$_3$), bismuth (V) oxide (Bi$_2$O$_5$), and mixtures thereof. Bismuth (III) oxide, however, is preferred, especially for those compositions employed in toluene dehydrocoupling reactions.

It will be noted, however, that while bismuth oxides, especially bismuth (III) oxide, are preferred for use in the present invention, the direct charging of bismuth oxides as starting materials is not necessary. Any compound of the desired bismuth such as salts, hydroxides, and the like, which are convertible by heat to the desired bismuth oxide, and as such, may be considered as a precursor thereof, may be used to provide indirectly the bismuth oxide for preparing the attrition resistant bismuth-containing metal/oxygen compositions of the present invention. Typical bismuth salts include the water-soluble nitrates, carbonates, and acetates.

The bismuth oxide component ranges in an amount from about 20 mole percent to about 65 mole percent, based on the total number of moles of bismuth oxide and alumina in the bismuth-containing metal/oxygen composition, and preferably from about 30 mole percent to about 55 mole percent. The alumina component makes up the remaining portion of the bismuth-containing metal/oxygen composition, which, in view of the stated mole percent of the bismuth oxide component, must range from about 35 mole percent to about 80 mole percent. Preferably, however, the alumina component constitutes from about 45 mole percent to about 70 mole percent of the bismuth-containing metal/oxygen composition.

Alumina concentrations greater and less than the stated 35 to 80 mole percent range, surprisingly, have been found to be detrimental. Compositions having alumina concentrations outside the stated range (35 to 80 mole percent) exhibit a marked decrease in attrition resistance, or stated differently, an increase in attrition rate. Lowered attrition resistance, of course, results in increased abrasion, breakage, and dusting of composition structures under high stress use conditions. Such abrasion, breakage, and dusting can cause undesirable pressure drop, flow problems, filter clogging, loss of fluidizability, and the like under such conditions, especially during operations employing fluidized bed reactor systems.

The attrition resistant bismuth-containing metal/oxygen compositions can be prepared in several ways. The simplest method involves intimately mixing at least one suitable bismuth oxide having a maximum mean particle size of about 100 $\mu$m with the desired alumina having a mean particle size from about 10 $\mu$m to about 200 $\mu$m such that the alumina/bismuth oxide mean particle size ratio is at least 2, in an amount sufficient to constitute from about 20 mole percent to about 65 mole percent of the composition. The bismuth oxide and alumina components may be dry mixed or mixed by slurrying in a suitable wetting agent (wet mixed), for example, water or an organic compound such as methanol, ethanol, and the like. When a wetting agent is employed in the mixing step, it is removed by heating the slurried mixture at a temperature and for a time sufficient to substantially remove the excess wetting agent. In general, heating at a temperature of about 150° C. to about 250° C., usually about 200° C., for about 1 hour to about 5 hours, usually 2 hours, is sufficient. It will be recognized, however, that the actual time and temperature will depend upon the particular wetting agent employed, the quantity of material, and the like. The dry mixed material may also be subjected to similar temperatures in order to remove any physically bound water. Continued heating of the dry mixture (from either the wet-mixed or dry-mixed components) at temperatures from about 250° C. to about 500° C. for about 1 hour to about 5 hours serves to decompose any salts which are present and remove other volatile components.

Upon completion of the drying and removal of any other volatile components, the dry mixture of bismuth oxide and alumina is calcined at a temperature of at least 0.4 T$_m$ for a time sufficient to cause the bismuth oxide and the alumina to infuse in accordance with diffusional behavior in metal oxides as described in Freer, *Journal of Material Science*, 15, 803–824 (1980) and undergo reaction to yield the attrition resistant bismuth-containing metal/oxygen compositions of the present invention. The calcination may be carried out in an inert atmosphere such as nitrogen, helium, and the like, or in air. In many instances, it may be desirable to conduct the initial calcination under an inert atmosphere in order to prevent oxidation of the bismuth ion of the bismuth oxide to a higher oxidation state which may prevent or severely curtail the necessary infusion. This initial calcination is then followed by a final calcination in air to form the desired bismuth-containing metal/oxygen composition.

As previously noted, the calcination is carried out by heating the dry mixture of bismuth oxide and alumina to a temperature of at least 0.4 $T_m$. It will be recognized that the actual temperature employed will depend primarily on the diffusional behavior of the bismuth oxide with the particular alumina. In a similar manner, the actual time employed will depend upon the component materials employed, as well as the calcination temperature. As an example, since alumina has a melting point ($T_m$) of about 2273° K. (2000° C.), temperatures typically from about 800° C. (0.47 $T_m$) to about 1400° C. (0.74 $T_m$) and a time from about 1 hour to about 15 hours or more are sufficient. Preferably, a temperature from about 900° C. to about 1100° C. and a time from about 8 hours to about 12 hours are employed, most preferably, a temperature from about 1000° C. to about 1050° C. and a time from about 10 hours to about 11 hours.

The calcination (and infusion) may be effected in any calcination apparatus known to the art. Non-limiting examples include ovens or muffle furnaces containing fixed beds or moving beds, rotary kilns, and the like.

In an alternative method of preparation, a suitable precursor hydroxide or salt of the bismuth oxide component such as a nitrate, carbonate, or acetate is intimately mixed with the alumina and infused and calcined as previously described. Another method involves the impregnation of the alumina with an aqueous solution of one or more of the precursor salts. Preferably, a high concentration of metal salt is employed in order to minimize the need for subsequent evaporation of solvent. After the impregnation, the resultant product is subjected to the infusion and calcining process as previously described.

2. Characterization of the Compositions

The attrition resistant bismuth-containing metal/oxygen compositions of this invention are substantially free of unreacted bismuth oxide and alumina as determined by x-ray diffraction (XRD). That is, the starting material components, under the heating and/or calcining conditions employed, have undergone infusion and reaction to an extent sufficient to preclude having the starting material components remain in an unreacted state. As a result, the compositions of the present invention are not simply active materials supported on a porous support material; they, instead, are novel compositions comprising the infusion and reaction product of an alumina and at least one bismuth oxide, all as previously defined.

The compositions of this invention exhibit excellent attrition resistance when compared to supported catalysts and compositions of the prior art. An attrition rate less than 0.5 weight percent/hour is, in general, preferred. In addition, the compositions demonstrate high activities, as well as high selectivities, in the many and varied transformations of organic compounds. In a preferred use embodiment, compositions prepared from bismuth (III) oxide and the previously described alumina have been found to be particularly efficacious as oxygen carriers and/or catalysts in the dehydrocoupling of toluene to stilbene and/or bibenzyl. Overall, and in general, bismuth and bismuth ions employed as catalysts in known prior art processes may be employed in the bismuth-containing metal/oxygen compositions of this invention in the same mode to effect similar reactions, but with the added advantage of increased attrition resistance.

The attrition resistance, calculated as the attrition rate in units of weight percent/hour is determined by an accelerated attrition test. In this test, which is described in detail in Example 3 below, the weight in grams of dust and fines generated via abrasion, friction, and breakage under stated conditions for a specified period of time, usually the 5–21 hour period (16 hours) out of a total of 21 hours, from a specified weight in grams of a sample of the bulk composition is measured. Using these values, the percent attrition during the specified period can be calculated as follows:

$$\% \text{ Attrition} = \frac{\text{Dust and Fines (5-21 Hour Period), g}}{\text{Initial Weight, g} - \text{Dust \& Fines (0-5 Hr. Period),}} \times 100$$

The attrition rate is then calculated as follows:

$$\text{Attrition Rate} = \frac{\% \text{ Attrition}}{\text{Time Period, Hours}}$$

It will be apparent, of course, that all things being equal with respect to properties exhibited by the bismuth-containing metal/oxygen compositions of this invention, the greater the attrition resistance (expressed as a smaller numerical attrition rate value in units of weight percent/hour), the more desirable such compositions become in that fewer difficulties associated with high rates of attrition (lack of attrition resistance) are experienced during use in reactions involving conditions of high stress. An attrition rate less than 0.5 weight percent/hour, as previously noted, for the compositions of this invention is preferred, with values of 0.3 weight percent/hour or less being most preferred.

The specific surface area value desirable for a given bismuth-containing metal/oxygen composition depends primarily on its intended use. As an example, compositions useful in the dehydrocoupling of toluene preferably will exhibit surface area values less than 5 m$^2$/g, with values from about 0.05 m$^2$/g and 1 m$^2$/g being most preferred. Such values result in greater activities and selectivities to the toluene dehydrocoupled products. Conversely, higher surface area compositions, especially those having surface areas greater than 5 m$^2$/g, exhibit decreased selectivities to the toluene dehydrocoupled products as evidenced by the undesirable tendency toward increased benzene and carbon dioxide production during such dehydrocoupling reactions.

The surface area of the bismuth-containing metal/oxygen compositions of this invention is measured according to the BET method [from Brunauer et al., *Journal of the American Chemical Society*, 60, 309–319 (1938)] described in ASTM D 3663-78 using a Micromeritics Digisorb 2500 instrument. In general, however, for samples having a relatively low surface area, for example, less than 5 m$^2$/g, krypton is preferably substituted for nitrogen as the adsorption gas for increased accuracy of measurement. Examples of metal/oxygen compositions of the invention may be represented by the empirical formula $BiO_x(Al_2O_3)_{0.93-1.15}$ wherein x is a number taken to satisfy the average valence of Bi in the oxidation state in which it exists in the composition.

3. Transformation of Organic Compounds

The attrition resistant bismuth-containing metal/oxygen compositions of this invention, as previously noted, are useful for the transformation of organic compounds in the vapor phase. For convenience and clarity, however, the use of the bismuth-containing metal/oxygen compositions will be described with reference to a process to oxidatively dehydrocouple toluene to produce toluene dehydrocoupled products, namely, stilbene and bibenzyl. As noted previously, such compositions preferably exhibit an attrition rate less than 0.5 weight percent/hour and, for use in the toluene dehydrocoupling process herein described, a surface area less than 5 $m^2/g$.

The attrition resistant bismuth-containing metal/oxygen compositions of this invention function in a catalytic mode, a stoichiometric mode as an oxidant or oxygen carrier, or a combined catalytic/stoichiometric mode for the dehydrocoupling of toluene.

In the catalytic mode of operation, oxygen or an oxygen-containing gas such as air or oxygen-enriched air is reacted with toluene in the presence of the attrition resistant bismuth-containing metal/oxygen composition in an amount sufficient for the dehydrocoupling reaction. In the stoichiometric mode of operation, the attrition resistant bismuth-containing metal/oxygen composition is the sole source of oxygen. That is, in the latter instance the dehydrocoupling of toluene is conducted in the substantial absence of added free oxygen such as would be obtained from air. In the combined catalytic/stoichiometric mode of operation, oxygen or an oxygen-containing gas is added as a reactant in a manner similar to that noted previously for the catalytic mode of operation. However, the amount of added oxygen is not sufficient for the dehydrocoupling reaction and the required additional oxygen must be supplied by the attrition resistant bismuth-containing metal/oxygen composition.

Of these three modes of operation, the stoichiometric mode is generally preferred in that undesirable side reactions—oxidative dealkylation, for example, to produce benzene and carbon dioxide—are substantially reduced. It will, of course, be recognized that in spite of the undesirability of producing benzene during the course of the toluene dehydrocoupling reaction, benzene is a valuable article of commerce. It is therefore highly desirable to recover the benzene values when substantial production thereof occurs. The recovery and purification of such benzene values may be accomplished by any standard method and means known to the art.

The term "dehydrocoupling" and related terms are employed herein to mean the toluene molecules are coupled or dimerized—with carbon-carbon bond formation occurring between the methyl group carbons—and the coupled molecules have lost either one or two hydrogen atoms from the methyl group of each toluene molecule. When two hydrogen atoms per molecule of toluene are lost, the carbon-carbon bond at the coupling or dimerization site is unsaturated as by dehydrogenation. That is, stilbene is the product. On the other hand, bibenzyl, having a saturated carbon-carbon bond at the coupling site, is the product when only one hydrogen atom per molecule of toluene is lost.

In general, the production of stilbene as the toluene dehydrocoupled product is preferred over the production of bibenzyl. This stated preference is due to the unsaturated character of stilbene as opposed to the saturated character of bibenzyl. And, as is well known in the art, the presence of the unsaturated olefinic carbon-carbon double bond causes the stilbene to exhibit high reactivity, thereby facilitating its direct use as an organic intermediate in numerous organic syntheses.

The toluene dehydrocoupling process using the attrition resistant bismuth-containing metal/oxygen compositions of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactant or reactants and the attrition resistant bismuth-containing metal/oxide composition. In general, a fluidized bed system is preferred in that it advantageously possesses the ability to approach isothermal conditions during the course of the reaction process. Moreover, the attrition resistant bismuth-containing metal/oxygen compositions of this invention are particularly suited for use in a fluidized bed system due to the low attrition rate and small particle size (mean particle size from about 10 $\mu$m to about 200 $\mu$m). It will be apparent, of course, that when using a fluidized bed system, fluid velocities (linear gas velocities) must be sufficient to maintain a uniform suspension of the particles of the attrition resistant bismuth-containing metal/oxygen composition, but insufficient to sweep the particles out of the reactor. Gas velocities in the range between about 1.52 cm/sec (0.05 ft/sec) to about 91.44 cm/sec (3.0 ft/sec) are usually sufficient, depending on factors such as the relative densities of the gas and solid, gas viscosity, the size and shape of the solid particles, the number of particles per unit volume (bed density), the size and configuration of the reactor, and the like.

Regardless of the particular type of reactor employed—whether fixed bed, moving bed, or a fluidized bed system—the reactant toluene will generally be heated and introduced to the reactor as a vapor. However, the reactant may be introduced to the reactor as a liquid and then vaporized.

The oxidative dehydrocoupling reaction is carried out in the vapor phase and under the influence of heat. The temperature range under which the reaction can be carried out ranges from about 450° C. to about 650° C. and preferably is conducted at from about 500° C. to about 600° C., most preferably at about 575° C.

Pressure is not critical in the toluene dehydrocoupling process of this invention. The reaction may be carried out at subatmospheric, atmospheric, or superatmospheric pressures as desired. It will be generally preferred, however, to conduct the reaction at or near atmospheric pressure. Generally, pressures from about $2.53 \times 10^4$ pascals or Pa (0.25 atmosphere or atm) to about $4.05 \times 10^5$ Pa (4.0 atm) may be conveniently employed.

The reaction time for the contact of the reactant with the attrition resistant bismuth-containing metal/oxygen compositions of this invention may be selected from a broad operable range which may vary from about 0.1 to about 60 seconds. The reaction time may be defined as the length of time in seconds which the reactant gases measured under reaction conditons are in contact with the attrition resistant bismuth-containing metal/oxygen composition in the reactor. The reaction time may vary depending upon the reaction temperature and the desired toluene conversion level. At higher temperatures and lower toluene conversion levels, shorter contact times are required. Generally, the contact time will vary from about 0.5 seconds to about 20 seconds. Preferably, for optimum conversion and selectivity in the preferred temperature range, a contact time from about 1 second to about 12 seconds is employed.

In addition to the toluene, other inert substances such as nitrogen, helium, and the like may be present in the reactor. Such inert materials may be introduced to the process alone or may be combined with the other materials as feed. Water or steam may be added to the reaction zone, preferably being introduced with the feed in order to improve the selectivity to the desired product(s) and particularly to suppress complete oxidation to $CO_2$. Steam/hydrocarbon mole ratios in the range from about 0.1 to about 10 or more are suitable, the upper limit being determined by practical cost considerations. Mole ratios in the range from about 0.5 to about 3 are preferred.

The attrition resistant bismuth-containing metal/oxygen compositions of this invention contain oxygen in such a manner that they are capable of releasing stoichiometric quantities of oxygen under the oxidative reaction conditions employed to dehydrocouple toluene as described hereinbelow. The oxygen in the compositions is associated with the metals as oxides, as oxygen complexes, or as mixtures of oxides and complexes.

As previously noted, the dehydrocoupling reaction may be conducted in the presence or absence of added free oxygen. When oxygen is not added to the system, that is, the reaction is conducted in the stoichiometric mode of operation, the oxygen required for the reaction is provided by the bismuth-containing metal/oxygen composition which enters into the reaction and is consequently reduced (or, in actual practice, partially reduced) during the course of the reaction. This necessitates regeneration or reoxidation which can be easily effected by heating the material in air or oxygen at temperatures from about 500° C. to about 650° C. for a period of time ranging from about 5 seconds to about 1 hour. In a semicontinuous operation, regeneration can be effected by periodic interruption of the reaction for reoxidation of the reduced composition, that is, periods of reaction are cycled with periods of regeneration. Operation, however, can be on a continuous basis whereby a portion of the attrition resistant bismuth-containing metal/oxygen composition can be continuously or intermittently removed, reoxidized, and the reoxidized material can thereafter be continuously or intermittently returned to the reaction. The latter method is particularly adapted to operations in which the attrition resistant bismuth-containing metal/oxygen composition is employed in the form of a moving bed or the preferred fluidized bed.

When oxygen is employed as a reactant, the reaction may be conducted in either a catalytic mode of operation or a combined catalytic/stoichiometric mode of operation, depending on the amount of oxygen supplied. In the catalytic mode of operation, oxygen is supplied in an amount sufficient for the dehydrocoupling reaction. The actual amount of oxygen supplied may be specified as a function of the amount of the toluene. On this basis, the amount of oxygen supplied is ordinarily selected to provide a toluene/oxygen mole ratio from about 1 to about 8 and preferably from about 2 to about 6.

In the combined catalytic/stoichiometric mode of operation, the amount of oxygen supplied as a reactant is not sufficient for the dehydrocoupling reaction, thereby requiring an additional source of oxygen. The required additional oxygen will be supplied by the attrition resistant bismuth-containing metal/oxygen composition, that is, the composition will serve as the additional source of oxygen. As a result, the attrition resistant bismuth-containing metal/oxygen composition enters into the reaction and is consequently reduced during the course of the reaction. This necessitates regeneration or reoxidation of the reduced composition which can be easily effected as described previously for the stoichiometric mode of operation.

In either mode of operation employing added oxygen as a reactant, whether catalytic or combined catalytic/stoichiometric, the added free oxygen may be supplied either as oxygen or an oxygen-containing gas such as air or oxygen-enriched air.

As previously indicated, the toluene dehydrocoupling process employing the attrition resistant bismuth-containing metal/oxygen compositions of this invention is preferably carried out in the absence of added free oxygen, that is, in the stoichiometric mode of operation, and utilizes only that oxygen supplied by the attrition resistant bismuth-containing metal/oxygen composition. Also, with few exceptions, at substantially comparable conditions, the lower the toluene conversion level, the higher will be the selectivity to the dehydrocoupled products. That is, under similar conditions, the selectivity to the dehydrocoupled toluene product is in general inversely proportional to the toluene conversion level. However, for practical reasons, the dehydrocoupling reaction will generally be conducted at a toluene conversion level of about 20 to about 55 percent.

The toluene dehydrocoupled products, stilbene and bibenzyl, may be recovered and purified by any appropriate method and means known to the art and further elucidation here will be unnecessary duplication of the art. As noted previously, stilbene, of course, is the preferred product.

The following specific examples illustrating the best presently known methods of practicing the invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

Alumina Preparation

The alumina was sieved for 30 minutes. The material less than 120 mesh (U.S. Standard Sieve Size; 125 $\mu$m) or 70 mesh (200 $\mu$m), as indicated, and larger than 400 mesh (38 $\mu$m), 325 mesh (45 $\mu$m), or 200 mesh (75 $\mu$m), as indicated, was retained. The retained material was sieved twice more on clean mesh screens of the previously indicated size. Each time the −120, +400 (120/400), −70, +325 (70/325), or −70, +200 (70/200) mesh material, as indicated, was retained. A sufficient quantity of the triply sieved alumina was accurately weighed for use in preparing the attrition resistant bismuth-containing metal/oxygen compositions.

Properties of numerous representative aluminas (Al$_2$O$_3$) are tabulated in Table 1.

used for illustrative purposes). The parameters for such compositions are set forth in Table 2, below.

Procedure A

To a 1.1-liter (1-quart, dry) wide-mouthed polyethyl-

TABLE 1

REPRESENTATIVE ALUMINAS AND PROPERTIES[1]

| SAMPLE NO. | BRAND IDENTIFICATION | CRYSTAL PHASE[2] INITIAL | CRYSTAL PHASE[2] AFTER 2 HR @ 550° C. | WATER (CHEMICAL) Wt. %[3] | PARTICLE SIZE DISTRIBUTION, %[4] μm <20 | 20-45 | 45-88 | 88-125 | >125 |
|---|---|---|---|---|---|---|---|---|---|
| 1-A | Alcoa FAH (SF-30)[11] | Boehmite and Gibbsite | α and χ | 6.5 | 11 | 3 | 25 | 28 | 33 |
| 1-B | Calsicat 49B-048A[12] | δ and θ | δ and θ | 1.0 | 5 | 26 | 52 | 13 | 4 |
| 1-C | Catapal SB[13] | α and Boehmite | α and γ | 14.5 | 12 | 20 | 36 | 22 | 10 |
| 1-D | Harshaw 1465p[14] | γ | γ | 2.0 | 9 | 24 | 49 | 12 | 6 |
| 1-E | Harshaw 3970p[14] | γ | γ | 2.4 | 2 | 22 | 44 | 22 | 10 |
| 1-F | Kaiser A-300[15] | χ | χ | 5.0 | 12 | 24 | 30 | 24 | 10 |
| 1-G | Ketjen D[16] | Boehmite | γ | 14.5 | 12 | 33 | 50 | 4 | 1 |
| 1-H | Ketjen M[16] | Boehmite | γ | 14.5 | 8 | 15 | 43 | 21 | 13 |
| 1-I | Norton SA6373[17] | Boehmite | γ | 12.0 | 12 | 11 | 20 | 44 | 13 |
| 1-J | Norton 74368[17] | Boehmite | γ | 7.0 | 2 | 35 | 55 | 15 | 5 |
| 1-K | Norton 74380[17] | Boehmite | γ and χ | 8.1 | 11 | 28 | 52 | 7 | 2 |
| 1-L | Alcoa F-1-100[11] | γ and Boehmite | γ | 14.8 | 7.5 | 22.5 | 40 | 23.7 | 6.3 |

| SAMPLE NO. | BET SURFACE AREA, m$^2$/g[5] | DENSITY, g/cc PARTICLE[6] | SKELETAL[7] | BULK[8] | POROSITY[9] FRACTIONAL[10] | % <55 Å[9] | MEAN PORE DIAMETER, Å[9] |
|---|---|---|---|---|---|---|---|
| 1-A | 151.5 | 1.78 | 3.27 | 1.23 | 0.455 | 76.1 | 37.5 |
| 1-B | 91.1 | 1.42 | 3.57 | 0.72 | 0.602 | 1.0 | 125.0 |
| 1-C | 226.0 | 1.15 | 3.48 | 0.99 | 0.670 | 16.3 | 67.5 |
| 1-D | 147.8 | 1.42 | 3.35 | 0.89 | 0.576 | 11.0 | 77.5 |
| 1-E | 196.5 | 1.18 | 3.56 | 0.86 | 0.669 | 14.5 | 72.5 |
| 1-F | 154.9 | 1.68 | 3.27 | 1.21 | 0.486 | 74.0 | 47.5 |
| 1-G | 257.4 | 1.04 | 3.29 | 0.90 | 0.684 | 44.0 | 57.5 |
| 1-H | 280.0 | 1.27 | 3.12 | 1.00 | 0.593 | 47.0 | 62.5 |
| 1-I | 235.0 | 1.38 | 3.65 | 0.94 | 0.622 | 42.1 | 57.5 |
| 1-J | 206.0 | 1.16 | 3.28 | 0.82 | 0.646 | 16.6 | 72.5 |
| 1-K | 186.0 | 1.60 | 3.075 | 0.80 | 0.480 | 80.0 | 57.5 |
| 1-L | 210.0 | 1.44 | 3.43 | 0.88 | 0.580 | 69.7 | 42.5 |

[1]Physical property measurements were performed on heat treated aluminas (after 2 hours at 550° C.).
[2]Analyses were performed using a Phillips Diffractometer.
[3]Determined by heating an accurately weighed sample to constant weight and by differential thermal analysis (DTA).
[4]Measured according to the manufacturer's procedure using a Leeds & Northrup Microtrak instrument.
[5]Measured according to ASTM D 3663-78 for surface area of catalysts using a Micromeritics Digisorb 2500 instrument.
[6]Measured by mercury displacement using an Aminco-Winslow Porisimeter.
[7]Determined using a Micromeritics Helium Pycnometer.
[8]Determined by accurately weighing a given volume of compacted material.
[9]Determined by nitrogen desorption using a Micromeritics Digisorb 2500 instrument.
[10]Calculated using the mathematical relationship, $F.P. = \dfrac{\rho_{He} - \rho_{Hg}}{\rho_{He}}$ where F.P. is the fractional porosity, $\rho_{He}$ is the skeletal density, and $\rho_{Hg}$ is the particle density.
[11]Available commercially from Aluminum Company of America, 1501 Alcoa Bldg., Pittsburgh, PA 15219.
[12]Obtained from Mallinckrodt, Inc., Calsicat Div., 1707 Gaskell Ave., Erie, PA 16508. Not commercially available. Included for comparative purposes.
[13]Available commercially from Conoco Chemicals Company, P. O. Box 2197, Houston, TX 77001.
[14]Available commercially from Harshaw Chemical Company, 1945 East 97th Street, Cleveland, OH 44106.
[15]Available commercially from Kaiser Chemicals Company, 300 Lakeside Dr., Oakland, CA 94643.
[16]Available commercially from Akzo Armak Company (Agent), 300 So. Wacker Dr., Chicago, IL 60606.
[17]Available commercially from Norton Company, 1 New Bond St., Worcester, MA 01606.

EXAMPLE 2

General

Attrition resistant bismuth-containing metal/oxygen compositions were prepared by intimately mixing the appropriate quantities of at least one bismuth oxide and an alumina, heating to a temperature and for a time sufficient to remove any added wetting agent and physically bound water, as well as other volatile components, and calcining the mixture. The calcined material was cooled under controlled cool-down conditions and sieved to the original size of the alumina. The retained material accounted for greater than 90 weight percent of the calcined bismuth-containing metal/oxygen composition. The bismuth-containing metal/oxygen compositions were further characterized as described in Examples 3 (attrition rate) and 4 (transformation of organic compounds, with the dehydrocoupling of toluene being used for illustrative purposes). The parameters for such compositions are set forth in Table 2, below.

Procedure A

To a 1.1-liter (1-quart, dry) wide-mouthed polyethylene jar was added 200.7 grams (0.43 mole) of bismuth (III) oxide (Bi$_2$O$_3$) powder and 2–3 1.9-centimeter (0.75-inch) diameter alumdum balls. The jar was placed on a ball mill and the contents ball milled for 6 hours. The ball-milled Bi$_2$O$_3$ powder and 97.2 grams (0.90 mole) of triply sieved 120/400 mesh alumina (Sample No. 1-F) were placed in a second polyethylene jar of the same size without the alumdum balls. The Al$_2$O$_3$/Bi$_2$O$_3$ mole percent ratio was 67.7/32.3. The jar was shaken by hand for 5 minutes and then rotated on a ball mill for 3 hours. The resultant mixture was passed through a 100 mesh (U.S. Standard Sieve Size) screen to insure mixing. Any clumps remaining on the screen were broken up and passed through the screen. The sieved mixture was returned to the jar and rotated on the ball mill an additional 3 hours if any clumps remained on the screen after sieving, or, in the absence of any remaining clumps, for only 0.5 hour to break up any stratification of powders resulting from sieving. The mixture was divided equally among three 7.62-centimeter (3.0-inch) diameter and 2.54-centimeter (1.0-inch) deep fused alumina dishes containing less than 0.2% silica and having a capacity of about 80 milliliters. The material was compacted to insure close physical contact. The shallow loading depth permitted air to diffuse the material located at the bottom of the dishes during the air calcination.

The loaded dishes were placed in an air-purged furnace and heated in air at 200° C. for 1 hour to remove any physically bound water, followed by 450° C. for 1 hour to remove any other volatile components, and then calcined at 850° C. for 5 hours. The bismuth-containing metal/oxygen composition was cooled at 700° C. at a maximum cool-down rate of 150° C. per hour. Thereafter, the cool-down was continued at its natural rate to ambient temperature.

The cooled, lightly agglomerated metal/oxygen composition was crushed and sieved for 30 minutes to complete the breakdown of the soft agglomerations to −120 mesh particles. The metal/oxygen composition was then heated in air at 200° C. for 1 hour to remove, respectively, any physically bound water and other volatile components, and recalcined at 850° C. for 1 hour and 1000° C. for 4 hours. Cool-down was carried out as previously described. The material was crushed and sieved for 30 minutes to complete the breakdown of the soft agglomerations to 120/400 mesh particles which particle size corresponds to the original particle size range of the alumina.

Procedure B

Procedure A, above, was repeated except that sufficient water was added to the dry-mixed components, with stirring by hand, to form a thixotropic paste. The paste was then loaded into the fused alumina dishes and dried and calcined as described in Procedure A.

Procedure C

Procedure A, above, was repeated except that after the initial heating, calcination, cool-down, and sieving, the metal/oxygen composition was heated at 200° C. for 1 hour, followed by 450° C. for 1 hour to remove, respectively, any physically bound water and other volatile components, and calcined at 650° C. for 1.5 hours, 850° C. for 1.5 hours, and 900° C. for 4 hours.

Procedure D

Procedure A, above, was repeated using 200.0 grams (0.43 mole) of $Bi_2O_3$ and 86.0 grams (0.80 mole) of 120/400 mesh $Al_2O_3$ (Sample 1-F). The $Al_2O_3/Bi_2O_3$ mole percent ratio was 65/35.

Procedure E

A metal/oxygen composition having an $Al_2O_3/Bi_2O_3$ mole percent ratio of 69.7/30.3 was prepared in accordance with Procedure A, above, using 186.4 grams (0.40 mole) of $Bi_2O_3$ and 98.4 grams (0.92 mole) of 120/400 mesh $Al_2O_3$ (Sample 1-F).

Procedure F

A metal oxygen composition having an $Al_2O_3/Bi_2O_3$ mole percent ratio of 66/34 was prepared in accordance with Procedure B, above, using 400.0 grams (0.86 mole) of $Bi_2O_3$ and 179.8 grams (1.67 moles) of 120/400 mesh $Al_2O_3$ (Sample 1-F).

EXAMPLE 3

This Example illustrates the accelerated attrition test used to determine attrition rate of the attrition resistant metal/oxygen compositions of this invention.

The apparatus used to determine attrition rate is described in *Houdry Catalyst Brochure*, Air Products and Chemicals, Inc., "FCC Catalyst Retention is Better with Houdry ® HFZ ™ & HEZ ™ Catalysts", 1977. It consisted of a stainless steel tube 69.85 centimeters (27.5 inches) in length and 3.81 centimeters (1.5 inches) in inside diameter connected through a cone [10.16-centimeter (4-inch) rise] to a stainless steel tube 45.72 centimeters (18 inches) in length and 12.7 centimeters (5 inches) in inside diameter which had a flanged opening at the upper end.

The upper end was capped with a 0.64-centimeter (0.25-inch) thick stainless steel plate having a tubular opening in the center 3.81 centimeters (1.5 inches) in length and 0.95 centimeter (0.38 inch) in inside diameter. The plate was bolted onto the flange through eight 0.48-centimeter (0.19-inch) diameter holes machined into its outer perimeter and sealed with a neoprene gasket. Attached to the center-tube opening was a 250-milliliter filter flask, which had an extraction thimble attached to its side arm. A perforated stainless steel plate containing three equally spaced 0.041-centimeter (0.016-inch) diameter holes was located at the bottom of the stainless steel tube. Connected to the bottom of the stainless steel tube was air inlet means containing pressure regulators and flow controllers. The filter flask and the extraction thimble assembly was conditioned by passing humidified air through it for 30 minutes and then weighed. A sample of the composition (from Example 2) was screened using a 125/400 mesh sieve (U.S. Standard Sieve Size) to remove any dust and fines. A 50-milliliter sample of the screened composition was accurately weighed and charged to the apparatus described above. Humidified air was introduced through the perforated plate at the bottom of the stainless steel tube at a linear velocity of about $3.048 \times 10^4$ cm/sec ($1 \times 10^3$ ft/sec) to fluidize the composition.

After 5 hours, the flask and thimble assembly (first flask and thimble assembly) was replaced with another conditioned flask and thimble assembly (second flask and thimble assembly). The first flask and thimble assembly was weighed to determine the weight in grams of dust and fines associated with weak particles, dust, and trash already present in the composition. The fluidization was continued for an additional 16 hours for a total of 21 hours. At the end of this period, the second flask and thimble assembly was weighed to determine the weight in grams of dust and fines resulting from attrition during the prolonged fluidization. The attrition rate, as weight percent/hour, was calculated as follows:

$$\% \text{ Attrition} = \frac{\text{Dust \& Fines (5-21 Hr. Period), g}}{\text{Initial Weight, g} - \text{Dust \& Fines (0-5 Hr. Period), g}} \times 100$$

$$\text{Attrition rate} = \frac{\% \text{ Attrition}}{\text{Time Period, Hours}}$$

The attrition rate is shown in Table 2 under the column headed "Attrition Rate, Wt. %/Hour."

TABLE 2

| EXAMPLE | METAL OXIDE(S) GRAMS (MOLES) | | MOLE % | MEAN PARTICLE SIZE, $\mu m^2$ | ALUMINA[1] GRAMS (MOLES) | MOLE % | PARTICLE SIZE, $\mu m^2$ RANGE | MEAN |
|---|---|---|---|---|---|---|---|---|
| 2-A | 200.7 (0.43) | $Bi_2O_3$ | 32.3 | 10 | 97.2 (0.90) 1-F | 67.7 | 38–125 | 97 |
| 2-B | " | | " | " | (0.90) 1-F | | " | " |
| 2-C | | " | | " | (0.90) 1-F | | " | " |
| 2-D | 200.0 (0.43) | " | 35.0 | " | 86.0 (0.80) 1-F | 65.0 | " | " |
| 2-E | 186.4 (0.40) | " | 30.3 | " | 98.4 (0.92) 1-F | 69.7 | " | " |
| 2-F | 400.0 (0.86) | " | 34.0 | " | 179.8 (1.67) | 66.0 | " | " |

| EXAMPLE | ALUMINA/METAL OXIDE(S) MEAN PARTICLE SIZE RATIO | PREPARATIVE CONDITIONS TEMPERATURE, °C./ TIME, HOURS DRYING | CALCINATION | METAL/OXYGEN COMPOSITION ATTRITION RATE[3] WT. %/HOUR | SURFACE AREA[4] $m^2/g$ | EMPIRICAL FORMULA[5] |
|---|---|---|---|---|---|---|
| 2-A | 9.7 | (1) 200/1[6] (2) 450/1[6] (4) 200/1[6] (5) 450/1[6] | (3) 850/5[6] (6) 850/1[6] (7) 1000/4[6] | 0.35 | 0.17 | $BiO_x(Al_2O_3)$ |
| 2-B | " | (1) 200/1[6] (2) 450/1[6] (4) 200/1[6] (5) 450/1[6] | (3) 850/5[6] (6) 850/1[6] (7) 1000/4[6] | 0.32 | 0.22 | " |
| 2-C | " | (1) 200/1[6] (2) 450/1[6] | (3) 650/1.5[6] (4) 850/1.5[6] (5) 900/4[6] | 0.30 | 0.15 | " |
| 2-D | 9.9 | (1) 200/1[6] (2) 450/1[6] (4) 200/1[6] (5) 450/1[6] | (3) 850/5[6] (6) 850/1[6] (7) 1000/4[6] | 0.63 | 0.20 | $BiO_x(Al_2O_3)_{0.93}$ |
| 2-E | " | (1) 200/1[6] (2) 450/1[6] (4) 200/1[6] (5) 450/1[6] | (3) 850/5[6] (6) 850/1[6] (7) 1000/4[6] | 0.22 | 0.20 | $BiO_x(Al_2O_3)_{1.15}$ |
| 2-F | " | (1) 200/1[6] (2) 450/1[6] (4) 200/1[6] (5) 450/1[6] | (3) 850/5[6] (6) 850/1[6] (7) 1000/4[6] | 0.29 | 0.15 | $BiO_x(Al_2O_3)_{0.97}$ |

[1]Alumina Sample No. from Table 1
[2]Measured according to the manufacturer's procedure using a Leeds & Northrup Microtrak instrument unless specified otherwise.
[3]Determined by the accelerated attrition test as described in Example 3.
[4]Measured according to ASTM D 3663-78 for surface area of catalysts using a Micromeritics Digisorb 2500 instrument.
[5]The empirical formula, for convenience only, is written showing alumina units associated with the remaining components. The alumina, however, is an integral component of the infusion and reaction product. Subscript "x" is a number taken to satisfy the average valences of the metal elements (excluding aluminum) in the oxidation states in which they exist in the compositions. [6]Air atmosphere.

EXAMPLE 4

A. Toluene Conversion Reactor

A stainless steel tube 38.1 centimeters (15 inches) in length and 1.27 centimeters (0.5 inch) outside diameter was employed as a fluidized bed reactor for the toluene conversion reaction. The tube was capped on the bottom by a conical section that had a 30° angle. The reactor was arranged vertically and equipped at the lower end with reactant inlet means for introducing the feed materials. The inlet means was fitted with a porous metal frit for gas dispersion. The reactor was equipped at the upper end with reaction effluent outlet means fitted with a 90 $\mu$m filter, for collecting the effluent or, alternatively, for direct introduction thereof via a gas sampling valve into a gas-liquid chromatograph for analysis. A radiant furnace divided into two compartments, an upper compartment and a lower compartment, was used as a heat source throughout the reaction period. The lower compartment maintained a constant temperature in the reaction zone while the upper compartment maintained a lower, albeit constant, temperature (approximately 450° C.) in the gas expansion zone. The temperature was measured with a thermocouple in a temperature well positioned inside the length of the reactor.

B. Toluene Conversion

The reaction was conducted in a stoichiometric mode of operation under fluidized conditions unless otherwise noted. The reactor was charged with approximately 15 milliliters of the attrition resistant metal/oxygen composition prepared as described in Example 2, above. The reactor was placed in the two-compartment radiant furnace and heated to the operating temperatures, usually 575° C. for the reaction zone, which temperatures were maintained throughout the reaction period. The reactor was operated at a pressure of 2.53×10⁵ pascal (2.5 atmospheres, 36.7 psia) in a four-step cycle which comprised (a) passing a stream of air through the attrition resistant metal/oxygen composition for a period of time ranging from 5 seconds to 1 hour, usually 30 minutes (composition oxidation or regeneration); (b) purging the system with a ½ mole ratio feed mixture of nitrogen and water for 1 minute (purge); (c) feeding a toluene/water mixture having a ½ mole ratio through the system for 3 minutes (toluene dehydrocoupling or composition reduction); and (d) purging the system as in step (b) (purge). The cycle was then repeated. The total molar feed rate during each step of the four-step cycle was maintained at 15-17 millimoles/minute (about 557 cc/minute) flow rate which, under reaction conditions, provided a linear gas velocity of about 8.23 centimeter/second (0.27 ft/sec) and a superficial reactor residence (contact) time of about 4 seconds unless specified otherwise. Samples of the reaction effluent were taken at 30-second intervals for analysis by gas-liquid chromatography. The results, integrated over the 3-minute dehydrocoupling step (c) period, are tabulated in Table 3.

TABLE 3

| METAL/OXYGEN COMPOSITION NO. | TEMPERATURE, °C./ SUPERFICIAL CONTACT TIME, SECONDS[1] | CONVERSION, MOLE % | SELECTIVITY, MOLE % | | |
|---|---|---|---|---|---|
| | | | TRANS-STILBENE | COUPLING[2] | BENZENE |
| 2-A | 575 | 11.0 | 47.7 | 81.2 | 11.9 |
|  | 560/7.4 | 38.0 | 62.0 | 79.1 | 12.6 |
| 2-B | 535/0.6 | 5.2 | 48.2 | 87.2 | 5.6 |
| 2-C | 570/0.6 | 6.7 | 45.8 | 79.6 | 8.1 |
| 2-D | 565/0.6 | 7.7 | 50.4 | 79.4 | 11.9 |
| 2-E | 590/1.2 | 7.6 | 34.6 | 78.6 | 15.5 |
| 2-F | 575/1.2 | 13.5 | 53.9 | 87.1 | 7.9 |

[1]A superficial contact time of about 4 seconds was employed in the fluidized bed toluene conversion runs unless specified otherwise.
[2]Selectivity to trans-stilbene + (cis stilbene + bibenzyl).

EXAMPLE 5

This procedure illustrates a method of separating the stilbene in pure form.

Collect product streams from a number of toluene dehydrocoupling reactions in dry ice chilled traps. Flash distill the combined streams to a 200° C. bottoms temperature and then batch distill through a 2.5-centimeter inside diameter × 99.0-centimeter long column packed with extruded metal. Collect the fraction having a boiling point at about 186° C./20 mm mercury as trans-stilbene. The stilbene product is a white, crystalline solid having a melting point of 124°–125° C. and a retention time identical with an authentic sample of trans-stilbene as determined by gas chromatographic coinjection.

Molten trans-stilbene reacts rapidly with atmospheric oxygen to form numerous oxygenated (or polar) impurities, a major constituent of which is benzophenone. As a result, molten trans-stilbene should be protected from exposure to the atmosphere. Trans-stilbene so contaminated can be purified by recrystallization from 95% ethanol to yield pure product.

Thus, it is apparent that there has been provided, in accordance with the present invention, attrition resistant metal/oxygen compositions, a process for preparing same, and a process for utilizing such compositions to transform organic compounds, for example, to dehydrocouple toluene to yield toluene dehydrocoupled products, that fully satisfy the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for dehydrocoupling toluene which comprises:
   (a) contacting the toluene in the vapor phase at a temperature from about 450° C. to about 650° C. with an attrition resistant bismuth-containing metal/oxygen composition comprising the infusion and reaction product of
      (i) 35 to 80 mole percent of an alumina existing in a crystal form consisting of $\gamma$, $\delta$, $\eta$, and $\chi$ crystal forms, and mixtures thereof, or that can be transformed by heat to such crystal forms, and characterized by
         (a) a mean particle size from about 10 $\mu$m to about 200 $\mu$m, and
         (b) a fractional porosity of at least 0.2,
         (c) a surface area of at least 150 m$^2$/g, and
         (d) a pore diameter such that at least 10 percent of the pores are less than 55 Å, and
      (ii) 20 to 65 mole percent of at least one bismuth oxide, or compound convertible by heat to such bismuth oxide, having a maximum mean particle size of about 100 $\mu$m with the proviso that the alumina/bismuth oxide mean particle size ratio is at least 2, which metal oxide is susceptible of undergoing infusion and reaction with with the alumina upon being subjected to temperatures of at least 0.4 T$_m$ for a time sufficient to cause infusion and reaction between the metal oxide and the alumina, wherein T$_m$ is the melting point in °K. of the alumina which composition exhibits a surface area of less than 5 m$^2$/g, and
   (b) recovering the toluene dehydrocoupled product.

2. The process of claim 1 wherein the mean particle size of the alumina is from about 20 $\mu$m to about 125 $\mu$m.

3. The process of claim 1 wherein the alumina has a fractional porosity from about 0.2 to about 0.8.

4. The process of claim 1 wherein the alumina particles are spheroidal.

5. The process of claim 1 wherein the alumina is a hydrated alumina selected from the group consisting of Boehmite, pseudo-Boehmite, Bayerite, and Gibbsite.

6. The process of claim 1 wherein the alumina/bismuth oxide mean particle size ratio is 15 or more.

7. The process of claim 6 wherein the bismuth oxide component concentration is in an amount from about 30 mole percent to about 55 mole percent.

8. The process of claim 1 wherein the bismuth oxide is selected from the group consisting of bismuth (III) oxide, bismuth (V) oxide, and mixtures thereof.

9. The process of claim 1 wherein the composition is represented by the empirical formula $$BiO_x(Al_2O_3)_{0.93-1.15}$$

wherein x is a number taken to satisfy the average valence of Bi in the oxidation state in which it exists in the composition.

10. The process of claim 1 wherein steam is introduced with the toluene in an amount sufficient to provide a steam/toluene mole ratio between about 0.1 and about 10.

11. The process of claim 1 wherein the contacting between the toluene and the attrition resistant bismuth-containing metal/oxygen composition is effected for a period between about 1 second and about 12 seconds.

12. The process of claim 11 wherein the temperature is between about 500° C. and about 600° C.

13. The process of claim 1 wherein the dehydrocoupling reaction is conducted in a stoichiometric mode of operation in the absence of added free oxygen.

14. The process of claim 1 wherein a reactant selected from the group consisting of oxygen and an oxygen-containing gas is introduced with the toluene.

15. The process of claim 14 wherein the oxygen and oxygen-containing gas is introduced in an amount sufficient to conduct the dehydrocoupling reaction in a catalytic mode of operation.

16. The process of claim 15 wherein the oxygen and oxygen-containing gas is introduced in an amount sufficient to provide a toluene/oxygen mole ratio between about 1 and 8.

17. The process of claim 14 wherein the oxygen and oxygen-containing gas is introduced in an amount sufficient to conduct the dehydrocoupling reaction in a combined catalytic/stoichiometric mode of operation.

18. The process of claim 1 wherein the dehydrocoupling reaction is conducted at a toluene conversion level of about 20 to about 55 percent.

19. The process of claim 32 wherein the surface area of the composition is from about 0.05 $m^2/g$ to about 5 $m^2/g$.

20. The process of claim 1 wherein the composition exhibits an attrition rate less than 0.5 weight percent/hour.

21. The process of claims 1, 2, 3, 4, 5, 6, 7, 8, 9, 10, 11, 12, 13, 14, 15, 16, 17, 18, 19, or 20 wherein the dehydrocoupled toluene product is stilbene.

* * * * *